United States Patent [19]

Takahashi et al.

[11] Patent Number: 4,942,255
[45] Date of Patent: Jul. 17, 1990

[54] METHOD FOR PRODUCING α-ASPARTYLPHENYLALANINE DERIVATIVES

[75] Inventors: Satoji Takahashi; Tadashi Takemoto, both of Yokkaichi, Japan

[73] Assignee: Ajinomoto Co., Inc., Tokyo, Japan

[21] Appl. No.: 301,445

[22] Filed: Jan. 25, 1989

[30] Foreign Application Priority Data

Feb. 5, 1988 [JP] Japan .................................. 63-23842
Jun. 21, 1988 [JP] Japan .................................. 63-152716

[51] Int. Cl.$^5$ ........................................ C07C 101/02
[52] U.S. Cl. ........................................ 560/41; 562/450
[58] Field of Search ........................... 560/41; 562/450

[56] References Cited

FOREIGN PATENT DOCUMENTS 61-212597 9/1986 Japan .................................. 560/41

*Primary Examiner*—Bruce Gray
*Attorney, Agent, or Firm*—Oblon, Spivak, McClelland, Maier & Neustadt

[57] ABSTRACT

A method for producing an α-aspartylphenylalanine derivative represented by formula (2), which comprises reacting a β-aspartylphenylalanine derivative represented by formula (1):

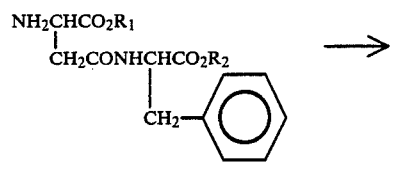

Formula (1)

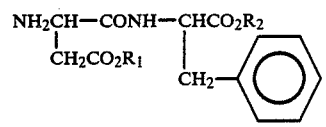

Formula (2)

with a basic compound in an alcohol solvent in the presence of a hydroxide, sulfate, chloride, carbonate or acetate of an element selected from the group consisting of zinc, copper, nickel, magnesium, aluminum, iron, tin, silicon and titanium, wherein $R_1$ and $R_2$ represent hydrogen or an alkyl group having 1 to 4 carbon atoms.

8 Claims, No Drawings

METHOD FOR PRODUCING α-ASPARTYLPHENYLALANINE DERIVATIVES

BACKGROUND OF THE INVENTION

1. Field of the Invention:

The present invention relates to a method for producing an α-aspartylphenylalanine derivative (hereafter simply referred to as an α-AP derivative) represented by formula (2), from a β-aspartylphenylalanine derivative (hereafter simply referred to as a β-AP derivative):

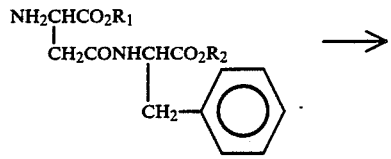

Formula (1)

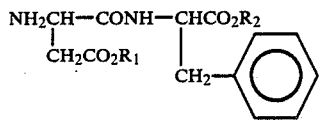

Formula (2)

wherein $R_1$ and $R_2$ represent hydrogen or an alkyl group having 1 to 4 carbon atoms.

2. Description of the Related Art:

For production of α-L-aspartyl-L-phenylalanine methyl ester (hereafter simply referred to as α-APM) useful as a novel sweetener, a variety of methods are known.

Among them, most of the methods comprise protecting the amino group of L-aspartic acid with a protecting group such as, for example, a carboxybenzoxy group, a formyl group, a hydrogen halide, etc., converting into the corresponding anhydride, condensing the anhydride with L-phenylalanine methyl ester to form N-protected L-aspartyl-L-phenylalanine methyl ester, then splitting the protecting group off to obtain α-APM. However, according to these methods, β-L-aspartyl-L-phenylalanine methyl ester (hereafter simply referred to as β-APM) is an unavoidable by-product.

On the other hand, a method is known (Published Examined Japanese Patent Application No. 277696/1986) for producing α-AP derivatives (formula (2)) and α-aspartylphenylalanine anhydride derivatives (hereafter simply referred to as DKP derivatives) from β-AP derivatives (formula (1)).

However, the yield of the desired α-AP derivatives is low and large quantities of by-products are produced. It is also disadvantageous in that large quantities of DKP derivatives are formed.

In the case of converting the DKP derivatives to the α-AP derivatives, its yield is poor and large quantities of by-products are also produced. For this reason, it is desired that the DKP derivatives not be formed. In order to solve this problem, it was extremely important to develop a technique for preventing the formation of DKP derivatives and to improve the yield of α-AP derivatives. That is, when the α-AP derivatives can be prepared from the β-AP derivatives in a high yield, such greatly contributes industrially since the α-AP derivatives can readily be converted to α-APM.

SUMMARY OF THE INVENTION

As a result of extensive investigation on a method of preparing the α-AP derivative from the β-AP derivative in a high yield, the present inventors have surprisingly found that when the β-AP derivative is reacted with a basic compound in an alcohol solvent in the presence of an inorganic compound of zinc, copper, nickel, magnesium, aluminum, iron, tin, silicon and/or titanium or an organic compound thereof, the α-AP derivative (formula (2)) can be prepared in an extremely high yield.

DETAILED DESCRIPTION OF THE PREFERRED EMBODIMENTS

According to the method of the present invention, undesired DKP derivatives are not formed or if any, are formed in an extremely small amount.

The α-AP derivative obtained according to the method of the present invention can easily be converted to the α-APM hydrochloride (hereafter simply referred to as α-APM.HCl) in a conventional manner, for example, when the α-AP derivative is present in an aqueous solution containing HCl and methanol (Published Unexamined Japanese Patent Application No. 129258/1984).

As the raw materials used in the present invention, β-AP derivatives shown by formula (1) can be used. Among them, β-aspartylphenylalanine dimethyl ester (the α-carboxyl group of the aspartic acid residue of β-APM is methyl-esterified; hereafter simply referred to as β-APM$_2$) and β-aspartylphenylalanine α-methyl ester (the α-carboxyl group of aspartic acid residue of β-aspartylphenylalanine is methyl-esterified; hereafter simply referred to as β-A(M)P) can be particularly advantageously used. There is no particular obstacle even though some α-AP derivatives are contained in addition to the raw material. As a matter of course, even though the β-AP derivative is in the form of HCl or sulfuric acid salts, the β-AP derivative can be used directly as the raw material.

For reference, the β-AP derivative shown by formula (1) can be obtained in a known manner. Among the β-AP derivative shown by formula (1), in the case where $R_1$ is hydrogen, the β-AP derivative can be obtained by converting the α-carboxyl group of aspartic acid into, for example, the benzyl ester, protecting the N-terminal with a protective group conventionally used, reacting with a phenylalanine alkyl ester in the presence of a condensing agent such as dicyclohexylcarbodiimide to convert into the N-protected aspartylphenylalanine alkyl ester and then removing the N-protective group and the benzyl ester group in a conventional manner.

Further in the case that $R_2$ of the α-AP derivative is hydrogen, the β-AP derivative can be obtained by using an alkyl ester of the α-carboxyl group of aspartic acid, protecting the N-terminal with a protective group conventionally used, reacting the α-carboxyl group with benzylated phenylalanine in the presence of a condensing agent as described above and then removing the N-protective group and the benzyl ester group in a conventional manner.

Further in the case that both $R_1$ and $R_2$ of the β-AP derivative are an alkyl group, the β-AP derivative can be obtained by condensing the N-protected aspartic acid having the alkyl esterified α-carboxyl group with a phenylalanine having the alkyl esterified α-carboxyl group in a similar manner and then removing the N-protective group.

Furthermore in the case that both $R_2$ and $R_3$ of the β-AP derivative are hydrogen, the β-AP derivative can be obtained by saponifying an alkyl ester of the three described above with an alkali.

The β-AP derivative which is N-protected with a formyl group, a hydrogen halide, etc. can be used as the N-protected β-aspartylphenylalanine alkyl ester (or dialkyl ester) without removing the N-protective group.

Next, conditions for forming the derivative of formula (2) from the derivative of formula (1) are described. The solvent is not particularly limited but preferably is an alcohol such as methanol, ethanol, propanol, isopropanol, butanol, etc. Of course, an organic solvent such as toluene, acetone, dichloroethane, methyl acetate, ethyl acetate, butyl acetate, a solvent mixture with water, etc. are also effective.

The inorganic and organic compounds to be added may be zinc, copper, nickel, magnesium, aluminum, iron, tin, silicon and/or titanium, ions thereof and compounds thereof. For example, the metals, etc. described above may be used directly but in this case, reaction with basic compounds in the presence of sulfuric acid or hydrochloric acid is more effective. Examples of the compounds include hydroxides such as zinc hydroxide, copper hydroxide, nickel hydroxide, magnesium hydroxide, aluminum hydroxide, iron hydroxide, etc.; inorganic salts such as zinc sulfate, zinc chloride, copper chloride, nickel chloride, copper sulfate, magnesium carbonate, magnesium sulfate, aluminum chloride, ferric sulfate, tin chloride, titanium chloride, etc.; organic salts such as zinc acetate, copper acetate, nickel acetate, aluminum acetate, basic aluminum acetate, etc.; compounds obtained by coordinating the aforesaid metals with chelating agents such as ethylenediaminetetraacetic acid, etc.; alcoholate such as zinc methylate, zinc ethylate, etc; and alkyl compounds thereof such as methyl, ethyl, etc. The aforesaid compounds may contain crystalline water. Further, the metals, etc. or ions thereof described above may also be retained on ion exchange resins or chelating resins or immobilized on membranes, etc.

The amount of the inorganic and organic compound to be used may vary depending upon its kind but is 0.01-fold mole or more based on the β-AP derivative. For economic considerations, an amount of 0.01 to 3.0 fold mole is appropriate.

The basic compound to be added is not particularly limited but mention may be made of organic bases such as triethylamine, pyridine, etc.; inorganic bases such as sodium hydroxide, potassium hydroxide, calcium hydroxide, sodium carbonate, sodium hydrogencarbonate, ammonia, etc.; hydroxides of magnesium, iron, aluminum, etc.; sodium acetate, sodium methylate, etc.

The amount of the basic compound to be used may vary depending upon kind but is generally 0.1 to 10-fold mole based on the β-AP derivative.

The reaction of the present invention is carried by mixing the aforesaid β-AP derivative, the alcohol solvent, the inorganic and organic compounds and the basic compound with or without stirring. In this case, the reaction temperature is generally chosen from a range of −30° C. to 150° C. When the temperature is too low, the reaction rate decreases; when the temperature is too high, side reactions such as polymerization, etc. occur. Therefore, a range from −20° C. to 100° C. is preferably appropriate. The reaction time may vary depending upon reaction temperature and kind or amount of the basic compound but is generally 10 hours or shorter The reaction is completed generally in an hour when a strongly basic compound such as sodium hydroxide, potassium hydroxide, sodium methylate, etc. is used as the basic compound.

According to the method of the present invention, the β-AP derivative can be converted into the α-AP derivative in an extremely high yield. Therefore, α-APM can be readily produced in a high yield. Further, no DKP derivative is produced in the reaction solution; or, if any, the DKP derivative is formed in an extremely small amount. In addition, the major by-product is the β-AP derivative so that the β-AP derivative can be recycled as the raw material of the present invention. The reaction can be completed in a short time in a high concentration of the β-AP derivative without heating the β-AP derivative at high temperature. Therefore, the cost of equipment can be greatly reduced. As described above, the present invention is extremely important for industrialization which leads to production of α-APM at low cost.

Hereafter the present invention will be described more concretely with reference to the examples but is not to be limited thereto.

EXAMPLES

Example 1

To 60 ml of methanol solution containing 3.08 g of β-APM$_2$ was added 1.4 g of zinc sulfate heptahydrate. The mixture was stirred. Then, the temperature was elevated to 20° C. and 10 ml of methanol solution of 1 mole/l potassium hydroxide was added to the system followed by reacting for 20 minutes. α-Aspartylphenylalanine dimethyl ester (the β-carboxyl group of aspartic acid of α-aspartylphenylalanine methyl ester was methyl esterified; hereafter simply referred to as α-APM$_2$) in the reaction solution was quantitatively determined by high performance liquid chromatography.

As a result, 66.1% of α-APM$_2$ was formed based on β-APM$_2$. The formation of the DKP derivative was a trace.

Example 2

Amounts of α-APM$_2$ and α-APM formed by reacting under conditions similar to Example 1 except for in the presence of additives shown in Table 1 in place of zinc sulfate heptahydrate were quantitatively determined. The results are shown in Table 1.

TABLE 1

| Run No. | Additive | (based on β-APM$_2$; fold mol) | Rate of α-APM$_2$ and α-APM (based on β-APM$_2$; %) |
|---|---|---|---|
| 1 | CuCl$_2$ | 0.5 | 64.4 |
|   | H$_2$O | 3.5 |  |
| 2 | Zn(CH$_3$CO$_2$)$_2$.2H$_2$O | 0.5 | 63.7 |
|   | H$_2$O | 2.0 |  |
| 3 | ZnCl$_2$ | 0.5 | 58.8 |
|   | ion exchange resin* | 50 |  |
| 4 | MgCO$_3$ | 0.5 | 40.5 |
| 5 | Al$_2$O(CH$_3$COO)$_4$.4H$_2$O | 0.5 | 45.4 |
| 6 | Fe$_2$(SO$_4$)$_3$.H$_2$O | 0.5 | 35.7 |

*"Diaion CR10" manufactured by Mitsubishi Chemical Industry Co., Ltd.

Example 3

To 29.4 g of β-APM were added 500 ml of methanol and 6.5 ml of 98 wt % H$_2$SO$_4$. The mixture was heated to reflux for an hour with stirring. Then, the reaction was further continued for 6 hours with stirring while adding 200 ml of methanol. To the reaction solution was added 5.0 g of zinc hydroxide was added. The mixture was kept at 20° C. and 250 ml of methanol solution containing 1 mol/l potassium hydroxide was added. The mixture was reacted for 2 minutes. A small amount was subjected to sampling for quantitative determination. As a result, 58.3% of α-APM$_2$ and 4.2% of α-APM, 68.4% in total, were formed based on β-APM. Formation of the DKP derivative was a trace and 12.2% of β-APM$_2$ remained.

Example 4

In Example 3, 10 g of sodium hydroxide was added in place of the methanol solution containing 1 mol/l potassium hydroxide. The mixture was reacted for 30 minutes.

As a result of quantitative determination of α-APM$_2$ and α-APM, 64.8% was formed in total.

Example 5

In Example 3, 49 g of 28 wt % sodium methylate was added in place of the methanol solution containing 1 mol/l potassium hydroxide. The mixture was reacted in a similar manner.

Based on β-APM, 67.9% of α-APM$_2$ and 2.5% of α-APM, 70.4% in total, were formed.

Example 6

To 60 ml of methanol solution containing 1.72 g of β-APM$_2$ HCl salt and 1.72 g of β-APM$_2$ HCl salt was added 0.55 g of zinc hydroxide. The mixture was stirred. Then, the temperature was made 10° C. and the mixture was added to 5.4 ml of 4 mol/l sodium hydroxide-methanol solution (dilution of 48 wt % NaOH aqueous solution with methanol) followed by reaction for 10 minutes Quantitative determination of α-APM$_2$ showed 2.61 g as α-APM$_2$ HCl salt.

Reference Example 1

The procedure was performed in a manner similar to Example 1 except that no zinc sulfate heptahydrate was added. The amount of α-APM$_2$ formed was 25.5%. Also, many by-products were formed.

Reference Example 2

The procedure was performed in a manner similar to Example 1 except that no zinc hydroxide was added. The amount of α-APM$_2$ formed was 26.0%.

Reference Example 3

The whole volume of the final reaction solution obtained in Example 3 was concentrated until the system became an oil. To the concentrate were added 42 ml of 35 wt % hydrochloric acid solution and water to make the whole volume about 150 ml. The mixture was stirred at 20° C. for 7 days and then stirred at 5° C. for 2 days. The precipitated APM.HCl crystals were separated by filtration and 300 ml of water was added to the crystals followed by neutralization with 10% Na$_2$CO$_3$ aqueous solution at a pH of 4.5. Then, the system was heated to 60° to 65° C. to dissolve. Activated charcoal, 0.2 g, was added and the mixture was stirred and then filtered. The filtrate was allowed to stand at 5° C. for 24 hours. The precipitated crystals were separated by filtration and dried under reduced pressure, whereby 14.1 g of crystals (47.9% based on β-APM) were obtained. The crystals were identified to be α-APM by analysis with high performance liquid chromatography.

What is claimed as new and desired to be secured by Letters Patent of the United States is:

1. A method for converting a β-aspartylphenylalanine derivative represented by formula (1) into an α-aspartylphenylalanine derivative represented by formula (2), which comprises:

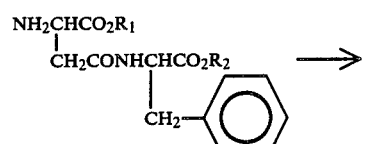

Formula (1)

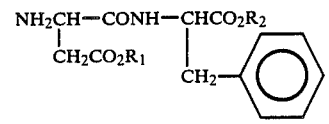

Formula (2)

reacting the compound of formula (1), wherein R$_1$ and R$_2$ are independently hydrogen or alkyl groups having 1 to 4 carbon atoms, with a basic compound and with a compound which is an hydroxide, sulfate, chloride, carbonate or acetate of an element selected from the group consisting of zinc, copper, nickel, magnesium, aluminum, iron, tin, silicon and titanium; in an alcoholic solvent wherein said alcohol is present in an amount sufficient to prevent precipitation of salts.

2. A method as claimed in claim 1, wherein R$_1$ and R$_2$ are each hydrogen or a methyl group.

3. A method according to claim 1, wherein said basic compound is selected from the group consisting of triethylamine, pyridine, sodium hydroxide, potassium hydroxide, calcium hydroxide, sodium carbonate, sodium hydrogen carbonate, ammonia, hydroxides of magnesium, iron, or aluminum, sodium acetate, and sodium methylate.

4. The method according to claim 3, wherein the amount of said basic compound is from 0.1 to 10 moles per mole of the derivative represented by formula 1.

5. The method according to claim 1, wherein the amount of the compound containing said element ranges from 0.01 to 3.0 moles per mole of said derivative represented by formula 1.

6. The method according to claim 1, wherein said alcohol is selected from the group consisting of methanol, ethanol, propanol, isopropanol, and butanol.

7. The method according to claim 1, wherein the compound containing said element is selected from the group consisting of copper chloride, zinc acetate, zinc chloride, magnesium carbonate, aluminum tetraacetate, and ferric sulfate.

8. The method according to claim 1, wherein the reaction temperature ranges from −30° C. to 150° C. and said reaction is carried out for from 0.5 to 10 hours.

* * * * *